United States Patent [19]

Violet

[11] 4,299,213

[45] Nov. 10, 1981

[54] LEG STABILIZER CONSTRUCTION

[76] Inventor: James T. Violet, 5238 Dungannon Cir. N.W., North Canton, Ohio 44720

[21] Appl. No.: 118,511

[22] Filed: Feb. 4, 1980

[51] Int. Cl.[3] .............................................. A61F 13/00

[52] U.S. Cl. .......................... 128/133; 128/DIG. 20; 269/328

[58] Field of Search ............... 128/133, 134, DIG. 20, 128/64; 269/328

[56] References Cited

U.S. PATENT DOCUMENTS

| | | | |
|---|---|---|---|
| 2,679,842 | 6/1954 | Brill | 128/134 |
| 2,991,785 | 7/1961 | Terrell | 128/134 |
| 3,027,895 | 4/1962 | Williams | 128/133 |
| 4,232,681 | 11/1980 | Tulaszewski | 128/133 |

FOREIGN PATENT DOCUMENTS

| | | | |
|---|---|---|---|
| 183896 | 7/1966 | U.S.S.R. | 128/64 |

*Primary Examiner*—John D. Yasko
*Attorney, Agent, or Firm*—Frease & Bishop

[57] ABSTRACT

A device which is adapted to be mounted on the edge of an operating table for holding a patient's thigh or upper leg in a fixed position on the table while arthroscopic surgery is being performed on the patient's knee. An inflatable member is secured on a first curved metal retention plate which is mounted on a flat metal portion of an angled base plate. The inflatable member is wrapped about the thigh of the patient and is secured thereon by fastening means. A second curved metal retention plate is adjustably mounted on the flat portion of the angled base plate opposite of the first retention plate. This second plate is moved into an adjusted position against the inflatable member diametrically opposite of the first retention plate to securely hold the patient's thigh and inflatable member between the pair of curved retention plates. Each retention plate provides an arcuate clamping surface slightly greater than the quadrant of an imaginary circle which is defined by the contours of the inner surfaces of the retention plates and patient's thigh. The inflatable member then is inflated, which securely grips the patient's thigh simultaneously with the inflatable member being securely clamped between the retention plates by its outward expansion. A downwardly projecting leg portion of the angled base plate then is inserted into a usual bracket mounted along the edge of an operating table to securely hold the thigh immobilized in the desired position on the table.

11 Claims, 12 Drawing Figures

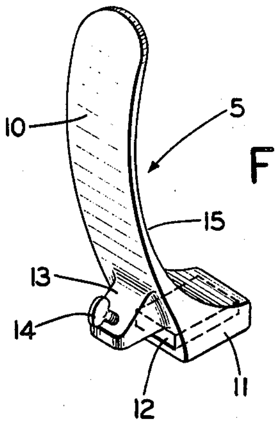
FIG. 6
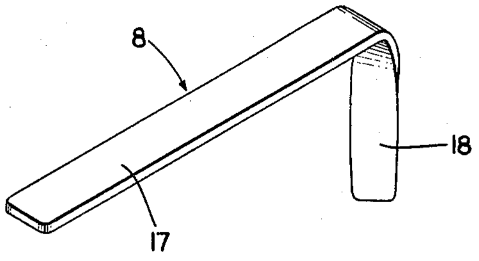
FIG. 7
FIG. 8
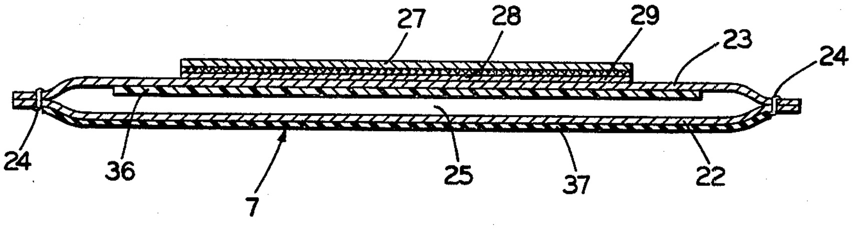
FIG. 9
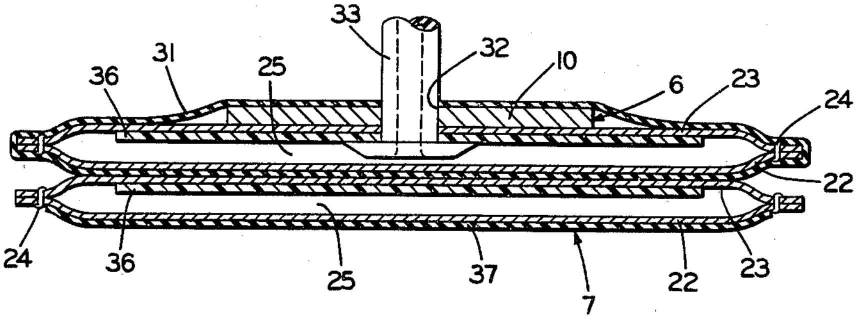
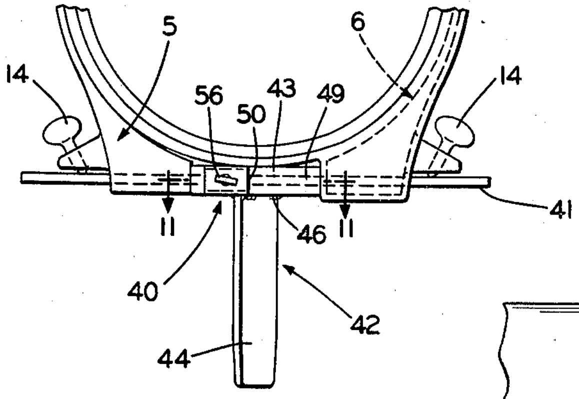
FIG. 10
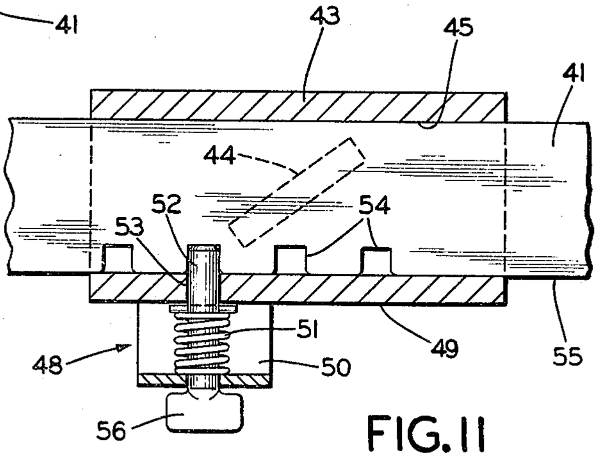
FIG. 11

LEG STABILIZER CONSTRUCTION

BACKGROUND OF THE INVENTION

1. Field of the Invention

The invention relates to a device for use by a surgeon for immobilizing a portion of a patient's limb during surgery. More particularly, the invention relates to a device for holding a patient's thigh in a fixed position on an operating table while enabling the lower portion of the leg to be bent and rotated at the knee when arthroscopic surgery is being performed on the patient's knee.

2. Description of the Prior Art

A relatively recent type of surgery, known as arthroscopic surgery, is becoming increasingly widespread in the medical field. In this type of surgery, an instrument called an arthroscope is inserted into various areas of a patient's body, in particular the joints, enabling the surgeon to view the interior of the joint. The surgeon then can view the joint for diagnostic purposes or for performing various surgical procedures within the joint by inserting instruments through small punctures made in the area of the joint.

Arthroscopic surgery is increasing in use in knee surgery for cartilage repair, spur and bone chip removal, and bone repair. During arthroscopic knee surgery, the surgeon by applying valgus and varus stress on the knee and by rotation of the knee can "gap" the bones within the knee to gain access to areas therebetween for performing surgery by the inserted instruments. It is critical that the upper leg or thigh area of the patient be completely fixed and immobile during the procedure so that this "gapping" is achieved entirely by movement of the lower portion of the leg. Heretofore, an assistant was required to manually hold the thigh of the patient during the arthroscopic surgery which may take the major portion of an hour. Such manual immobilization is extremely tiresome for the assistant and does not achieve the desired immobility of the patient's thigh.

There is presently available for use by arthroscopic surgeons a clamp for holding the patient's thigh, which consists of a metal strap which is clamped tightly about the patient's thigh by a toggle mechanism. Such device has been found to be unsatisfactory due to its bulkiness, expense, unsatisfactory gripping ability, and possible injury to the area of the leg which is gripped by the metal strap. Also, this known stabilizing device is believed to increase the possible contamination risks.

Various other devices have been developed for holding the limb of a patient during surgery, or the taking of X-rays, or during other medical procedures, such as shown in U.S. Pat. Nos. 2,266,231, 2,850,342, 4,045,678, and 4,069,813. Again, these types of clamps or immobilizing devices are not believed to be entirely satisfactory for holding a patient's thigh immobile in the desired position if used in arthroscopic surgery.

Accordingly, the need has existed for an improved device which is of a relatively simple, inexpensive, sanitary construction which can grip the thigh of a patient and retain the same in fixed immobile position on an operating table to permit movement of the lower leg by the surgeon during anthroscopic surgery. There is no known device of which I am aware which accomplishes this result in the manner of my invention which is described below and set forth in the appended claims.

SUMMARY OF THE INVENTION

Objectives of the invention include providing a leg stabilizer construction which is adapted to be mounted on the edge of an operating table by existing operating table clamps which are used for other procedures, thereby eliminating the need for special components which must be attached to the operating table or for modifying existing operating tables now in use in most hospitals; providing such a leg stabilizier which uses an inflatable member for clamping engagement about a patient's thigh, which type of clamping device has proven entirely effective, safe and satisfactory for applying pressure to parts of a patient's body, and in which the inflatable member is secured between a pair of curved metallic retention plates, and in which the retention plates are readily available components used for other applications during surgery; providing such a leg stabilizer in which at least one of the curved retention plates is adjustably mounted on a base plate which enables the leg stabilizer to accommodate various size thighs without affecting the holding and immobilizing effect of the device; providing such a leg stabilizer in which the inner thigh contacting surface of the inflatable member has a thin covering of surgical rubber which enhances the holding ability of the device to prevent slipping or rotation of the thigh, and to prevent injury to the patient's skin at the clamped area; providing such a leg stabilizer which can be placed on the patient's thigh before the patient is "prepped," thereby reducing possible contamination; providing such a leg stabilizer in which the inflatable member can be deflated easily during surgery enabling the thigh area to be rotated to a new position if required, whereupon the member can be reinflated to resecure the leg without removing or loosening any of the clamping straps or retention plates, and in which the inflatable member provides a large area of uniform clamping pressure around the leg for satisfactorily clamping and holding all thigh sizes; providing such a leg stabilizer which provides a more effective, less expensive device than is believed possible with existing leg clamps and stabilizers, and which solves problems, satisfies needs and obtains new results in the art.

These objectives and advantages are obtained by the improved leg stabilizer construction for holding the thigh area of a patient's leg in a fixed position on an operating table, the general nature of which may be stated as including an inflatable member adapted to encircle the thigh of a patient; a base plate adapted to be mounted on an operating table; and a pair of curved retention plates mounted on the base plate and engageable with generally diametrically opposite arcuate portions of the inflatable member, with at least one of the retention plates being adjustably mounted on the base plate to adjust the diametric spacing between said plates.

BRIEF DESCRIPTION OF THE DRAWINGS

A preferred embodiment of the invention—illustrative of the best mode in which applicant has contemplated applying the principles—is set forth in the following description and shown in the accompanying drawings, and is particularly and distinctly pointed out and set forth in the appended claims.

FIG. 6 is a perspective view of one of the curved retention plates of the improved leg stabilizer;

FIG. 7 is a perspective view of the angled base plate removed from the retention plates of the improved leg stabilizer;

FIG. 8 is a greatly enlarged sectional view taken on line 8—8, FIG. 3;

FIG. 9 is a greatly enlarged sectional view taken on line 9—9, FIG. 3;

FIG. 10 is a fragmentary front elevational view of a modified base plate for mounting the leg stabilizer on an operating table;

FIG. 11 is an enlarged fragmentary sectional view taken on line 11—11, FIG. 10.

Similar numerals refer to similar parts throughout the drawings.

DESCRIPTION OF THE PREFERRED EMBODIMENT

Figure 1:
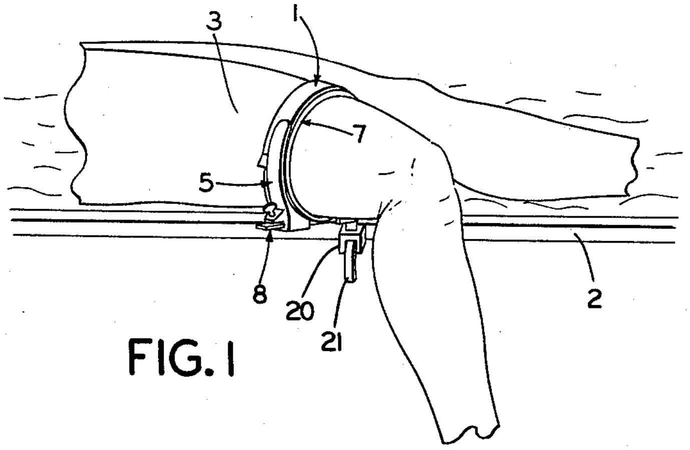
FIG. 1 is a fragmentary diagrammatic perspective view of the improved leg stabilizer construction holding a patient's thigh in a fixed position on an operating table.
Figure 5:
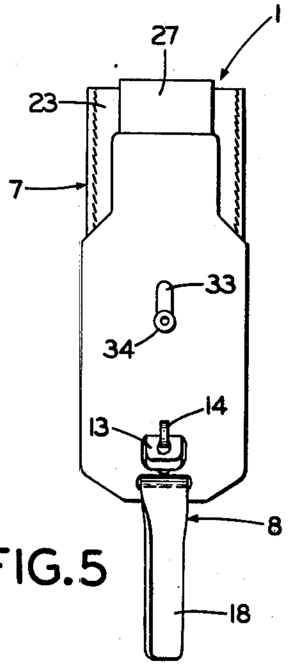
FIG. 5 is a right-hand end elevational view looking in the direction of arrows 5—5, FIG. 3.
Figure 4:
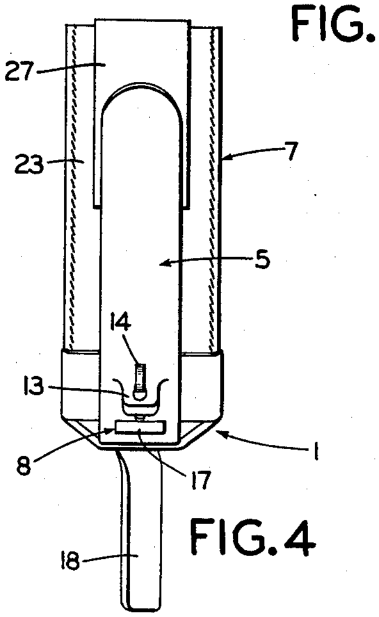
FIG. 4 is a left-hand end view looking in the direction of arrows 4—4, FIG. 3.

The improved leg stabilizer construction is indicated generally at 1, and is shown in FIG. 1 mounted on the edge of an operating table 2 securing and immobilizing the thigh area 3 of a patient who is reclining on the table. Leg stabilizer 1 is shown in partially assembled position in FIG. 2 and in assembled position in FIGS. 3–5, without the patient's leg being shown therein. Stabilizer 1 includes as its main components a pair of curved metal retention plates 5 and 6, an inflatable member 7, and a generally L-shaped angled base plate 8.

Figure 12:
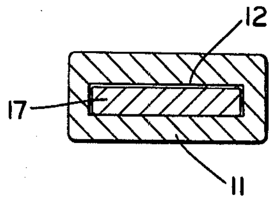
FIG. 12 is an enlarged fragmentary sectional view taken on line 12—12, FIG. 3.

Retention plates 5 and 6 are similar to each other and therefore only one is described in detail and shown in FIG. 6. Plates 5 and 6 are similar to a type of surgical equipment referred to as a "kidney plate," and therefore are readily available components which eliminates any additional expensive manufacturing procedures for the fabrication of leg stabilizer 1. Retention plate 5 includes a relatively flat curved portion 10 terminating in a lower base 11. Base 11 is formed with a rectangular-shaped opening 12 extending horizontally therethrough, as shown in FIGS. 6 and 12. A rearwardly extending lug 13 is formed integrally with curved portion 10 adjacent base 11. A thumbscrew 14 extends through a threaded opening formed in lug 13 for clamping plate 5 on base plate 8. Curved portion 10 has a curved elliptical-shaped inner surface 15 which has an arcuate length slightly greater than the quadrant of a circle. An arcuate length of approximately 97° has been found to be satisfactory for each plate 5 and 6.

L-shaped base plate 8 (FIG. 7) includes a flat horizontal strip portion 17 having a rectangular cross-sectional configuration complementary to that of retention plate openings 12 (FIG. 12), and a leg portion 18 formed integrally with flat plate 17 at one end thereof and extending downwardly at a right angle. Leg 18 preferably has an angle of twist of 35° with respect to flat plate portion 17 so as to position leg stabilizer 1 at the desired angle with respect to the edge of operating table 2 when mounted thereon, as shown in FIG. 1. Base plate 8 also is a known type of equipment used in conjunction with an operating table, which reduces the cost of stabilizer 1.

When mounting stabilizer 1 on table 2, leg 18 is inserted within an opening of a usual bracket 20 attached to the edge of operating table 2 and is secured therein by a clamping lever 21 (FIG. 1). Bracket 20 is of a type of bracket already available on many operating tables for attaching various other operating clamps and equipment on table 2 in addition to base plate 8. Thus, no special attachment mechanisms or table modifications are required for the use of improved stabilizer 1.

Figure 2:
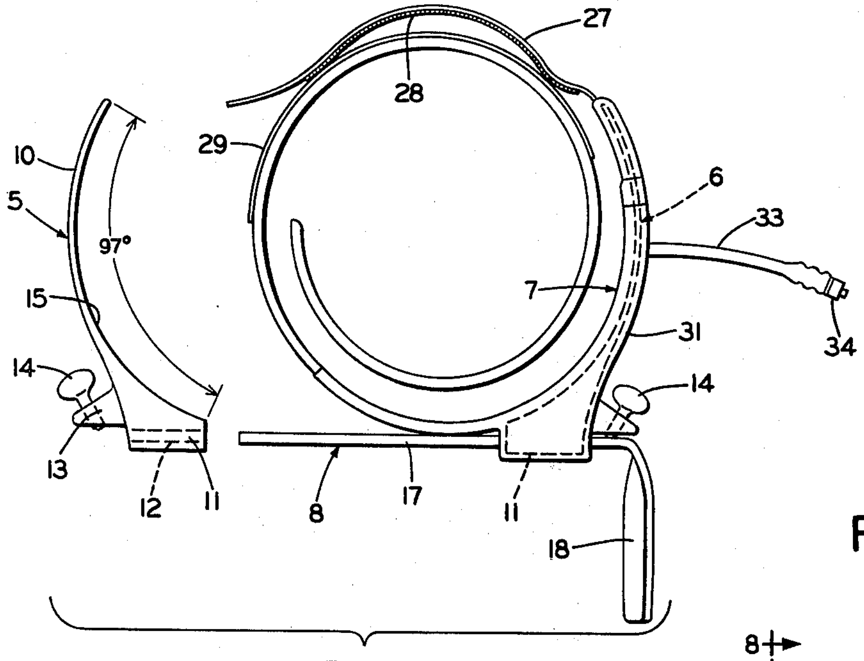
FIG. 2 is an enlarged partially exploded front elevational view of the leg stabilizer shown in FIG. 1.
Figure 3:
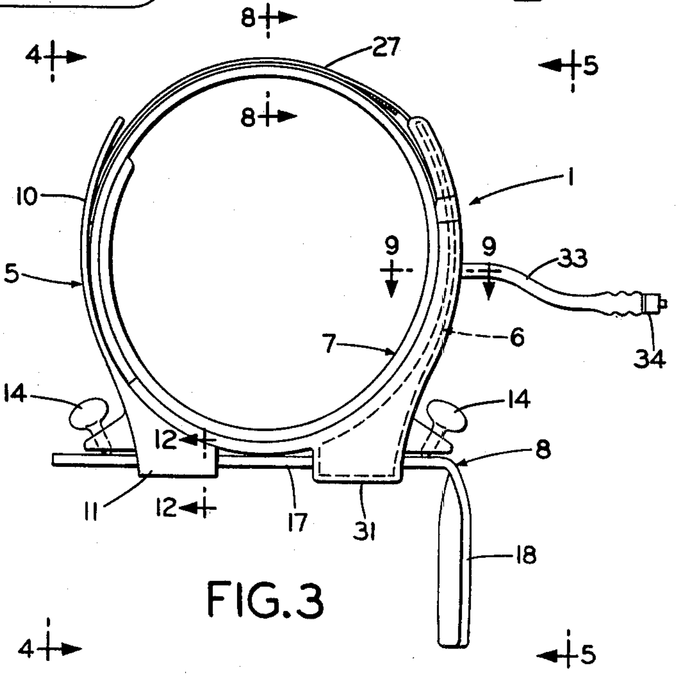
FIG. 3 is a front elevational view similar to FIG. 2, showing the leg stabilizer in assembled position.

Inflatable member 7 is shown in FIGS. 2 and 3 in assembled position with retention plate 6, and in greatly enlarged sectional views in FIGS. 8 and 9. Member 7 is similar in many respects to a usual type of surgical equipment referred to as a pneumatic tourniquet. Member 7 is formed by inner and outer strips 22 and 23 of an air-impervious material which are connected along their edges by seals 24 (FIG. 8) to form an elongated air chamber 25 therebetween.

A flexible strap 27 is attached to one end of inflatable member 7 (FIG. 2) and has a strip 28 of one portion of a self-engaging hook-and-loop material mounted thereon which is engageable with a strip 29 of complementary mating material which extends along a portion of the outer strip 23 of member 7 for securing member 7 in a wrapped configuration about a patient's thigh 3. The preferred hook-and-loop material is of the type known by the trademark VELCRO. Other types of fastening means than the above-described hook-and-loop material could be used, although this fastening means has been found to be most satisfactory.

In accordance with one of the features of the invention, retention plate 6 is attached to and incorporated with inflatable member 7 to form a main portion of improved leg stabilizer 1. Plate 6 is shown assembled with inflatable member 7 by a covering 31 (FIG. 9) which extends about plate 6 and the adjacent portions of member 7 to secure member 7 in a fixed position on retaining plate 6. The particular choice of such covering material is not critical to the invention, and if desired, member 7 can be attached to retention plate 6 by means other than covering 31.

Plate 6 is formed with a slot 32 (FIGS. 3, 5 and 9) through which a stem 33 of an air valve 34 extends for use in inflating or deflating member 7 by supplying air to or removing air from chamber 25. A flexible stiffening member 36 (FIGS. 8 and 9), preferably formed of a continuous strip of plastic material, is mounted within the major portion of air chamber 25. Stiffener 36 has a preformed coil-like configuration in order to bias member 7 toward the coiled arrangement as shown in FIG. 2 to facilitate the wrapping of member 7 about the thigh of a patient before inflating the same.

In accordance with another feature of the invention, a thin strip of surgical type rubber 37 or other nonslip material is applied to the surface of inner strip 22 to provide a nonslip engagement with the skin of a patient's thigh when member 7 is wrapped thereon. Rubber strip 37 also reduces irritation to the patient's skin in the contacted area.

When used in performing arthroscopic surgery, retention plate 6 and attached inflatable member 7 are secured by thumbscrew 14 on flat plate portion 17 of base plate 8 (FIG. 2). Inflatable member 7 then is wrapped about the patient's thigh and fastened by hook-and-loop coverings 28 and 29. Retention plate 5 then is moved horizontally along plate portion 17 of base plate 8 into abutting engagement with a diametrically opposite portion of inflatable member 7, as shown in FIG. 3. Thumbscrew 14 is tightened against flat plate 17 to securely position retention plate 5 on plate 17 and in abutting engagement with inflatable member 7.

Member 7 is inflated to a predetermined pressure by injecting compressed air into air chamber 25 from a compressed air supply through stem 33 of air valve 34. Inflatable of member 7 will securely clamp and hold the patient's thigh within the loop formed by member 7 simultaneously with clamping of member 7 within spaced retaining plates 5 and 6 by the outward expansion of member 7.

When leg stabilizer 1 is used during arthroscopic surgery on a patient's left knee instead of the right knee as shown in FIG. 1, L-shaped base plate 8 (FIG. 7) will be replaced by a similar component except that leg portion 18 will be angled or twisted in the opposite direction with respect to flat plate portion 17 to correctly position the leg stabilizer and patient's leg on the opposite side of the operating table. Thus, right-hand and left-hand base plates 8 are required for the mounting of stabilizer 1 on both sides or edges of operating table 2.

FIGS. 10 and 11 show a modified form of a base plate which replaces the L-shaped base plate 8 shown particularly in FIG. 7 and described above. The improved base plate is indicated generally at 40, and includes a horizontal, elongated flat metal plate 41 which is similar in size and configuration to flat plate portion 17 of L-shaped plate 8. Plate 41 is slidably inserted through openings 12 of retention plates 5 and 6 to adjustably mount plates 5 and 6 thereon to regulate the diametric spacing between concave surfaces 15 to accommodate the various sizes of patient's thighs.

A T-shaped mounting standard, indicated generally at 42, having a top cross member 43 and a vertically extending post 44 adjustably mounts plate 41 on the edge of operating table 2. Cross member 43 is a rectangular-shaped housing having an opening 45 (FIG. 11) extending horizontally therethrough for slidably receiving flat plate 41. Post 44 is mounted on the bottom surface of cross member 43 by welds 46 or other attachment means and is positioned at an angle of 35°, as shown in FIG. 11, corresponding to the angle or twist of leg portions 18 of L-shaped base plates 8 to properly position leg stabilizer 1 on the edge of the operating table.

A spring-biased plunger, indicated generally at 48, is mounted on a side wall 49 of cross member 43 for securing horizontal plate 41 in an adjusted position within opening 45 of cross member 43. Plunger 48 includes a mounting bracket 50 in which a compression coil spring 51 is located and telescopically mounted on a plunger rod 52. Rod 52 projects through an opening 53 formed in cross member wall 49 and is selectively engageable into a complementary-shaped notch 54, a plurality of which are formed along edge 55 of plate 41. A thumb tab 56 is provided on the opposite end of plunger rod 52 for manually disengaging the plunger end from within a selected notch 54 to reposition plate 41 within cross member opening 45.

Retention plates 5 and 6, including inflatable member 7, will be adjustably positioned on plate 41 by thumb screws 14 in a similar manner as described above with respect to flat plate portion 17 of L-shaped base plate 8.

Improved leg stabilizer construction 1 has a number of advantages not believed possible with existing stabilizers. Right and left-hand L-shaped base plates 8, retention plates 5 and 6, and inflatable member 7 are existing components used for other surgical procedures. Therefore, these components are readily available items which eliminates the need for the manufacture of any special components, thereby reducing the cost of the assembled construction. Inflatable member 7 preferably is attached to one of the retention plates, although it is possible that inflatable member 7 be wrapped about a patient's limb and placed within the curved concave surfaces 15 without being attached to either retention plate. The outward expansion of outer strip 23 of inflatable member 7 would be sufficient to clamp member 7 between the retention plates simultaneously with the gripping of the patient's thigh, even if member 7 is not physically attached to one of the retention plates. The inner lining of inflatable member 7 with rubber covering 37 provides a nonslip surface which contacts the patient's skin to enhance the gripping effect of member 7 in addition to preventing injury to the patient's skin at the gripped area. Another advantage of the improved leg stabilizer is the ability to reposition a patient's thigh within the stabilizer during the surgery without loosening or readjusting strap 27 of inflatable member 7 or retention plates 5 and 6. Air is removed from air chamber 25, which will relax the gripping effect of inflatable member 7 on the patient's thigh, enabling the thigh to be slightly rotated or moved within retention plates 5 and 6. Air chamber 25 then is reinflated, securely gripping the thigh in its new position.

Another advantage of leg stabilizer 1 is its placement on the patient's thigh before the leg is "prepped" and draped, reducing the risk of contamination. Also, stabilizer 1 eliminates the need of an assistant manually holding the patient's thigh in an immobilized position and permits the surgeon to apply the various stresses and movements on the knee joint to achieve the desired "gapping" more easily and efficiently than heretofore possible. Stabilizer 1 is easily adjusted for all thigh sizes by horizontal movement of retention plate 5 along flat plate portion 17 of mounting base plate 8. The arcuate lengths of the diametrically opposite concavely curved surfaces 15 of plates 5 and 6, each of which is slightly more than a quadrant of an imaginary circle, provides sufficient retaining and gripping area engageable with outer strip 23 of inflatable member 7 to securely grip the patient's thigh within the contour of inflatable member 7 simultaneously with the securing or clamping of member 7 between retention plates 5 and 6 by the outward expansion of air chamber 25 when member 7 is inflated.

Accordingly, the leg stabilizer construction is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding, but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved leg stabilizer construction is constructed and used, the characteristics of the construction, and the advantageous, new and useful results obtained; the new and useful structures, devices, elements, arrangements, parts, and combinations, are set forth in the appended claims:

I claim:

1. A device for immobilizing a portion of a patient's limb on a supporting platform, said device including:

(a) an elongated, inflatable, flexible member having a hollow interior forming an air chamber, said member being adapted to be wrapped about the limb of a patient for securely grasping the limb therein when the member is inflated;

(b) valve means communicating with the air chamber for introducing air into said chamber for inflating the flexible member;

(c) fastening means engageable with the flexible member for securing said member in a wrapped position about the limb of a patient prior to inflating said member;

(d) a base adapted to be mounted on the supporting platform closely adjacent the limb to be immobilized; and (e) a pair of rigid retention plates mounted in a spaced relationship on the base, each of said plates having a concavely curved inner surface abuttingly engaged with the flexible member to securely hold said member therebetween when the member is inflated, said curved surfaces being diametrically opposed with respect to each other and each forming generally a quadrant of an imaginary circle extending about the inflatable member.

2. The construction defined in claim 1 in which the inflatable member includes inner and outer strips of material joined together to form the air chamber therebetween; and in which a rubber covering is attached to the inner strip of material of the inflatable member to provide a nonslip surface adapted to contact the patient's limb being immobilized.

3. The construction defined in claim 1 in which an opening is formed in one of the retention plates; and in which the valve means includes a stem which extends through the opening of said one retention plate and communicates with the air chamber.

4. The construction defined in claim 1 in which the retention plates are similar to each other; and in which the concavely curved inner surface of each plate has an arcuate length of approximately 97°.

5. The construction defined in claim 1 in which at least one of the curved retention plates includes a lower portion having a horizontally extending opening formed therein; in which the base plate includes an elongated member complementary in cross-sectional configuration to the opening of the lower portion of said one retention plate; and in which the elongated member extends through said opening to slidably adjustably mount said one retention plate on said elongated member.

6. The construction defined in claim 5 in which screw clamping means is mounted on the lower portion of said one curved retention plate and is engageable with the elongated member of the base plate to clamp said one retention plate in position adjacent a patient's thigh.

7. The construction defined in claim 1 in which flexible stiffening means is located within the air chamber of the inflatable member to bias said inflatable member toward a coiled configuration.

8. The construction defined in claim 7 in which the flexible stiffening means is a flat strip of plastic material having a preformed coiled configuration.

9. The construction defined in claim 1 in which the inflatable member fastening means includes strips of complementary self-engaging hook-and-loop material.

10. The construction defined in claim 1 in which the base plate includes a flat strip of metal formed with a plurality of notches along an edge thereof, and a T-shaped standard formed with a horizontal cross member and a vertical post; in which the pair of retention plates are slidably adjustably mounted on the flat strip of metal; in which an opening is formed in the horizontal cross member; and in which the flat metal strip of the base plate is slidably adjustably mounted in the cross member opening.

11. The construction defined in claim 10 in which spring-biased plunger means is mounted on the cross member of the T-shaped standard and is selectively engaged with one of the notches of the flat metal strip to adjustably mount said strip and retention plates on said standard.

* * * * *

UNITED STATES PATENT AND TRADEMARK OFFICE

CERTIFICATE OF CORRECTION

PATENT NO. : 4,299,213

DATED : November 10, 1981

INVENTOR(S) : James T. Violet

It is certified that error appears in the above-identified patent and that said Letters Patent are hereby corrected as shown below:

Column 4, line 50, add -air- after "from" and before "chamber"

Column 5, line 12, change "Inflatable" to -Inflation-

Column 8, line 10, delete "plate"

Column 8, line 21, change "thigh" to -limb-

Column 8, line 33, delete "plate"

Column 8, line 40, delete "plate"

Signed and Sealed this

*Thirteenth* Day of *April 1982*

[SEAL]

*Attest:*

GERALD J. MOSSINGHOFF

*Attesting Officer* *Commissioner of Patents and Trademarks*